United States Patent
Flandre et al.

(10) Patent No.: US 7,943,394 B2
(45) Date of Patent: May 17, 2011

(54) METHOD AND DEVICE FOR HIGH SENSITIVITY DETECTION OF THE PRESENCE OF DNA AND OTHER PROBES

(75) Inventors: Denis Flandre, Brussels (BE); Luis Moreno Hagelsieb, Zapopan (MX); Rémi Pampin, Antony (FR); David Bourgeois, Papignies (BE); José Remacle, Malonne (BE); Pierre-Emmannuel Lobert, Somain (FR)

(73) Assignee: Université Catholique de Louvain, Louvain la Neuve (BE)

( * ) Notice: Subject to any disclaimer, the term of this patent is extended or adjusted under 35 U.S.C. 154(b) by 1193 days.

(21) Appl. No.: 10/519,014

(22) PCT Filed: Jun. 24, 2003

(86) PCT No.: PCT/BE03/00109
§ 371 (c)(1),
(2), (4) Date: Dec. 21, 2004

(87) PCT Pub. No.: WO04/001403
PCT Pub. Date: Dec. 31, 2003

(65) Prior Publication Data
US 2005/0227373 A1    Oct. 13, 2005

(30) Foreign Application Priority Data
Jun. 24, 2002   (EP) .................................... 02447122

(51) Int. Cl.
*G01N 33/566* (2006.01)
(52) U.S. Cl. ............ 436/501; 436/63; 436/98; 436/104; 436/111; 422/82.01
(58) Field of Classification Search .................. 436/501, 436/63, 98, 104, 111; 422/82.01
See application file for complete search history.

(56) References Cited

U.S. PATENT DOCUMENTS
5,917,264 A  *  6/1999  Maruno et al. ................ 310/309
(Continued)

FOREIGN PATENT DOCUMENTS
EP            0 402 917 A2      12/1990
(Continued)

OTHER PUBLICATIONS
S-J. Park, T.A. Taton and C.A. Mirkin, Science 295: 1503-1506, 2002.*
(Continued)

*Primary Examiner* — In Suk Bullock
*Assistant Examiner* — Timothy G Kingan
(74) *Attorney, Agent, or Firm* — Clark & Elbing LLP

(57) ABSTRACT

The present invention provides a method for capacitive detection of the presence of target sample on a substrate, which comprises the steps of: binding a target sample to selective binding sites on the substrate, the target sample being directly or indirectly labeled with conductive labels, and sensing the presence of the bound conductive labels to a binding site to thereby determine the presence of the target sample. The sensing step is carried out by a capacitive detection of the presence of the conductive labels. The present invention also provides a capacitive sensor device for determining the presence of a target sample. Conductive labels are directly or indirectly couplable to the target sample. The capacitive sensor device comprises a substrate having attached thereto a binding site able to selectively bind a target sample, a capacitive sensor element, and sensing circuitry for determining the presence of a target sample bound to the binding site by application of electrical signals to a capacitive sensor element. The capacitive sensor element comprises a set of at least two electrodes with non-conductive surfaces in a region associated with the binding site.

8 Claims, 7 Drawing Sheets

U.S. PATENT DOCUMENTS

| | | | |
|---|---|---|---|
| 5,922,537 A * | 7/1999 | Ewart et al. ........................ | 435/6 |
| 6,236,096 B1 * | 5/2001 | Chang et al. ................ | 257/419 |
| 6,514,394 B1 * | 2/2003 | Vangrunderbeek et al. .. | 204/400 |
| 6,627,154 B1 | 9/2003 | Goodman et al. | |
| 6,682,936 B2 * | 1/2004 | Kovacs ........................ | 436/149 |
| 2001/0053522 A1 | 12/2001 | Makino et al. | |
| 2002/0005580 A1 | 1/2002 | Goodman et al. | |
| 2002/0050173 A1 * | 5/2002 | Taguchi et al. ................. | 73/753 |
| 2002/0098119 A1 | 7/2002 | Goodman et al. | |
| 2002/0166764 A1 | 11/2002 | MacPhee | |
| 2003/0096321 A1 | 5/2003 | Remacle et al. | |
| 2003/0124522 A1 | 7/2003 | Remacle et al. | |
| 2003/0136960 A1 | 7/2003 | Goodman et al. | |
| 2009/0084162 A1 * | 4/2009 | Besnard et al. ............. | 73/31.06 |
| 2009/0273354 A1 * | 11/2009 | Dhirani et al. ................ | 324/663 |
| 2009/0273356 A1 * | 11/2009 | Pampin et al. ................ | 324/693 |

FOREIGN PATENT DOCUMENTS

| | | |
|---|---|---|
| EP | 1 516 174 B1 | 12/2007 |
| JP | 62 01967 | 1/1987 |
| JP | 2002 174611 | 6/2002 |
| WO | WO 90/05300 | 5/1990 |
| WO | WO 97/21094 | 6/1997 |
| WO | WO 99/07879 | 2/1999 |
| WO | WO 99/08105 | 2/1999 |
| WO | WO 00/72018 A1 | 11/2000 |

OTHER PUBLICATIONS

C. Berggren, B. Bjarnason and G. Johansson, Electroanlaysis 13(3): 173-180, 2001.*

P. Van Gerwen et al., International Conference on Solid-State Sensors and Actuators Chicogo, Jun. 16-19, p. 907-910, 1997.*

T.A. Taton, C.A. Mirkin and R.L. Letsinger, Science 289: 1757-1760, 2000.*

M. DeSilva et al., Biosensors and Bioelectronics 10: 675-682, 1995.*

PCT International Search Report (PCT/BE03/00109), Oct. 2003.

PCT International Preliminary Examination Report (PCT/BE03/00109), Jan. 2004.

Moreno-Hagelsieb et al., "Electrical Detection of DNA Hybridization: Three Extraction Techniques Based on Interdigitated $Al/Al_2O_3$ Capacitors," *Biosensors and Bioelectronics* 22:2199-2207 (2007).

Official Communication issued in connection with EP 03 760 533.4, dated Aug. 19, 2005.

Reply to Official Communication issued in connection with EP 03 760 533.4, dated Jan. 26, 2006.

Official Communication issued in connection with EP 03 760 533.4, dated May 24, 2006.

Reply to Official Communication issued in connection with EP 03 760 533.4, dated Dec. 4, 2006.

* cited by examiner

Concentrations
Up to Down :

- 20 nMol   (sample 3)
- 0.2 nMol  (sample 2)
- witness   (sample 1)

*Dashed* = average in
the air

METHOD AND DEVICE FOR HIGH SENSITIVITY DETECTION OF THE PRESENCE OF DNA AND OTHER PROBES

CROSS REFERENCE TO RELATED APPLICATIONS

This application is the U.S. National Stage of International Application No. PCT/BE2003/000109, filed Jun. 24, 2003, which was published in English under PCT Article 21(2), and which claims the benefit of European patent application 02447122.9, filed Jun. 24, 2002.

TECHNICAL FIELD OF THE INVENTION

The present invention relates to a method and apparatus for sensing of the presence of a molecular species or substance bound to a binding site, especially by means of conductive labels. In particular it relates to apparatus and methods for capacitive detection of binding of biological molecules on a micro-array or biochip.

BACKGROUND OF THE INVENTION

The introduction of micro-arrays or biochips is revolutionising the analysis of DNA (desoxyribonucleic acid), RNA (ribonucleic acid), proteins, other molecules, e.g. herbicides and pesticides, or other micro- or nanomaterials, e.g. microcarriers such as beads. Applications are, for example, human genotyping (e.g. in hospitals or by individual doctors or nurses), bacteriological screening, biological and pharmacological research.

Biochips, also called biosensor chips, biological microchips, gene-chips or DNA chips, consist in their simplest form of a substrate on which a large number of different probe molecules are attached, on well defined regions on the chip, to which molecules or molecule fragments that are to be analysed can bind if they are matched. The degree of match which is required to obtain a positive result can be controlled by the stringency of the binding, i.e. in how far conditions are applied which force only perfect matches or allow partial matches. For example, a fragment of a DNA molecule can bind to one unique complementary DNA (c-DNA) molecular fragment. The occurrence of a binding reaction can be detected, e.g. by using fluorescent markers that are coupled to the molecules to be analysed. This provides the ability to analyse small amounts of either a low number or a large number of different molecules or molecular fragments in parallel. One biochip can hold assays for 100 or even 1000 or more different molecular fragments. The technique can be extended to micro- and nanomaterials such as beads by attaching relevant molecules to the beads.

It is predicted and desired that biochips will become a mass produced product. Technology driving applications are, for example, an inexpensive method for rapid diagnostics, regardless of the test site, i.e. not only in hospitals and specialised laboratories but also at remote sites such as doctors' practices, accident locations and for the prevention or control of terrorist activities, and to reduce of the overall cost of disease management.

There is a large variety of known methods which measure the global reaction of hybridisation of all the DNA strands at one area of the biochip simultaneously, by a change of either optical reflection or transmission, or by a change of conductivity, by a change of the electrochemical state of the test system, or by a change of permittivity of the DNA medium. Some of these known methods measure a property due to the hybridised DNA itself and some due to specific hybridisation markers or labels.

One method for electronically detecting binding of sample molecules to probe molecules has been described in WO 00/72018. Spots with a spot size of at least 100 µm containing millions of capture complementary DNA single strands (complementary to a target DNA) are fixed to a glass slide. After the DNA probe hybridisation by the target DNA strand, the hybridised DNA is marked by gold nanoballs, around which silver (Ag) is precipitated in the presence of hydroquinone. The silver precipitates are detected by optical means as a change of reflectivity or transmissivity at the level of each spot. The external optical detection of a specific opaque label such a silver is limited by the resolution of low cost scanners: the spots must be larger than 100 µm. The labels must at least be much larger than 600 nm to be detectable with the visible spectrum used by the scanners. The detection is global at the spot scale and the sensitivity, i.e. the range of the detected grey scale, hardly exceeds 1:100.

Park et al. describe in the article "Array-based electrical detection of DNA with nanoparticle probes", Science, 22 Feb. 2002, vol. 295, p. 1503-1506, a spot of DNA single strands being grafted to a SiO2 layer (which has been thermally grown on Si) between two thin, bare gold electrodes spaced by a gap of 20 µm. After the DNA probe hybridisation by the target DNA strand, the hybridised DNA is marked by gold nanoballs, around which silver (Ag) is precipitated by hydroquinone. The electrical resistivity of the Ag precipitates (i.e. the real component of its impedance) is measured by applying a DC current between the two electrodes and measuring the resulting voltage difference at the spot scale again. In order to be able to perform the measurement, a user has to wait at least until a silver bridge forms between the two electrodes. To detect low amounts of DNA it is necessary to wait a long time, e.g. 35 minutes, to allow time for the silver precipitate to grow sufficiently to make a conductive path. However, precipitation of silver is also initiated by the bare gold electrodes, so when the bridge finally has been formed, it is not sure whether this is because silver has been precipitated on one or a plurality of gold nanoballs, or whether just a short-circuit between the electrodes has been formed by silver precipitation on the electrodes. These processes lead to the possibility of false positive readings. The conductivity measurement also depends on the gold electrode-to-silver layer contact resistance, which is not well known, nor very stable or reproductive. With this known technique, processing time is quite long, quantitative detection can be imprecise and a calibration prior to measurement is impossible, that is it is not possible to calibrate to a definite positive result level. Indeed, the negative result level is the equivalent resistance between the electrodes when no silver bridge is present which can be almost infinite before silver precipitation, and it takes a number of minutes (e.g. 5) of silver precipitation in hydroquinone to get the first short-circuit path between the widely spaced electrodes. The resistance, therefore, decreases by several orders of magnitude to a value whose absolute value is difficult to interpret making hybridised DNA quantification, difficult. Further, it takes an additional number of minutes (e.g. 20) to reduce the resistance still further, e.g. by three or more orders of magnitude. The resulting global range of current variation may be of 6 orders of magnitude from no silver to full silver precipitation, but the effective range from first short-circuit path to full short-circuit is much lower. This may provide a good signal to noise ration for an indication of hybridisation, but deriving further information from the shape of the curve or from the absolute resistance values is difficult.

Ideally, the measurement electrodes and electronics should be incorporated into a single, small device, i.e. onto an integrated circuit chip. For a resistive measurement, the use of noble metals, such as gold (Au) or Platinum (Pt) for the electrodes is required because they do not degrade in biological processes. However, these materials are hardly compatible with conventional integrated circuit fabrication. A number of barriers need to be provided between the metal and the semiconductor material on which the detector is fabricated, in order to avoid that the metal diffuses into the semiconductor material, thus leading to contamination and degradation of the active devices in the semiconductor circuits. Furthermore, the processing of the semiconductor chip and the application of the noble metal has to be done in separate clean rooms (to avoid cross-contamination between processes), which makes the fabrication of such detector chips more complex and expensive.

Also, a major limitation related to the use of hybridised DNA alone (no labels or markers to assist) concerns the sensitivity since the methods can generally only detect a change of a factor of 100% at the maximum, between single strand DNA probe (in case of no hybridisation) or hybridised DNA (i.e. two strands only instead of one). The detection of permittivity changes between two electrodes due to DNA binding alone is also limited by the sensitivity, which is hardly more than a few tens of percents.

SUMMARY OF THE INVENTION

It is an object of the present invention to provide a method and a device for measuring the presence of target molecules or materials, especially target biological molecules and materials, as fast as possible, and preferably as soon as a very low amount of the target molecule or material is present.

It is a further object of the present invention to provide a method and device for measuring the presence of target molecules or materials, especially target biological molecules and materials, with a large sensitivity of about 1:1000000.

It is yet another object of the present invention to allow quantification of the measurement of the presence of target molecules or materials, especially target biological molecules and materials.

It is yet another object of the present invention to limit the time required for measuring the presence of target molecules or materials, especially target biological molecules and materials, and hence improve the usefulness or to reduce cost.

The present invention is based on the surprising fact that a resistive measuring technique, in which a chemically formed metal bridge is to be measured, is not so advantageous because what is measured is generally the highest resistance part of the metal bridge (a local spot where the metal bridge has the smallest cross-section). This resistance value relates only to the way the metal bridge forms and does not provide any firm quantitative indication about the amount of target material present.

The above objectives are accomplished by a method and a device according to the present invention:

The present invention provides a method for capacitive detection of the presence of target sample on a substrate, which comprises:

binding a target sample to selective binding sites on the substrate, the target sample being directly or indirectly labelled with conductive labels, and sensing the presence of the bound conductive labels to a binding site to thereby determine the presence of the target sample. The sensing step is carried out by non-ohmic contacting, capacitive detection of the presence of the conductive labels.

Before the binding step, a preliminary capacitance measuring step may be carried out. The preliminary capacitance may be compared with the capacitance measured during the sensing step. Capacitance may be measured as function of frequency to obtain a value representative of a electrical resistive property of the conductive label. Also, a global impedance may be measured and the real part of the global impedance may be used in addition to the capacitive part to obtain more information.

The labels may be formed or enlarged prior to or during the sensing step, for example by metal, especially silver precipitation.

A method according to the present invention may furthermore comprise a step of optical detection of the presence of the label and/or a step of magnetic detection of the presence of the label and/or a step of detection of radioactive emissions from the label. The label may be magnetisable or magnetic, or it may shield an external magnetic field.

The present invention also provides a capacitive sensor device for determining the presence of a target sample. Conductive labels are directly or indirectly couplable to the target sample. The capacitive sensor device comprises a substrate able to selectively bind a target sample or having attached thereto a binding site able to selectively bind a target sample, a capacitive sensor element, and sensing circuitry for determining the presence of a target sample bound to the substrate or binding site by application of electrical signals to a capacitive sensor element. The capacitive sensor element comprises a set of at least two electrodes with non-conductive surfaces in a region associated with the binding site.

According to a preferred embodiment, the electrodes are made from a non-noble metal of which aluminium is only one example. The non-conductive surfaces can be formed by passivation, oxidation, nitridation or by depositing an insulating substance such as a paint of lacquer or similar insulating coating. If the metal is aluminium the insulating material may be alumina.

Preferably, the intercapacitance value of the electrodes changes when detecting the presence of conductive labels at least when coupled to the target sample.

According to one embodiment of the present invention, the set of electrodes may be an array of parallel fingers which can be individually addressed in pairs. The set of electrodes may be interdigitated electrodes with parallel fingers, all fingers related to one electrode being short-circuited. The set of electrodes may be an array of crossed fingers whose intersections can be individually addressed in pairs. The set of electrodes may be a matrix of point electrodes.

According to another embodiment, a third electrode may be provided insulated from the set of at least two electrodes, enabling the measurement of a second set of capacitive values. The substrate may comprise a semiconductor layer.

The presence of a conductive label may create a gate of a MOS or EEPROM like structure, which structure is embedded in the semiconductor below the binding test sites.

According to an embodiment of the present invention, the distance between the electrodes is reduced to a dimension comparable with the size of a single label. The distance between two electrodes may be 5 μm or less, preferably 2 μm or less.

A device according to the present invention may furthermore comprise a comparator unit, the outputs of the first and second capacitive sensing elements or first and second groups of capacitive sensing elements being fed to a comparator unit.

A device according to the present embodiment may furthermore comprise an optical detector for determining the presence of the target sample. It may also comprise a magnetic sensor or a radiation detector such as a Geiger counter for determining the presence of the target sample.

The term "micro-array" or "biochip" refers to generated arrays on one or more planar surfaces that constitute a plurality of discrete reaction or incubation compartments identifiable by their locations, e.g. as defined by geometrical co-ordinates on the array. Such arrays are suitable for use in assays for assessing specific binding characteristics between members of specific binding pairs. The arrays may be addressable arrays.

These and other features and advantages of the present invention will become apparent from the following detailed description, taken in conjunction with the accompanying drawings, which illustrate, by way of example, the principles of the invention.

BRIEF DESCRIPTION OF THE DRAWINGS

in FIG. 15A the length of the sensor device is 2 µm and the results are shown after 2 minutes 30 seconds of hybridisation; in FIG. 15B the length of the sensor device is 6 µm and the results are shown after 2'30" of hybridisation; and in FIG. 15C the length of the sensor device is 4 µm and the results are shown after 2 minutes 30 seconds of hybridisation (samples 1 and 3) and after 2 minutes of hybridisation (samples 5 and 6).

DESCRIPTION OF ILLUSTRATIVE EMBODIMENTS

Figure 1A:
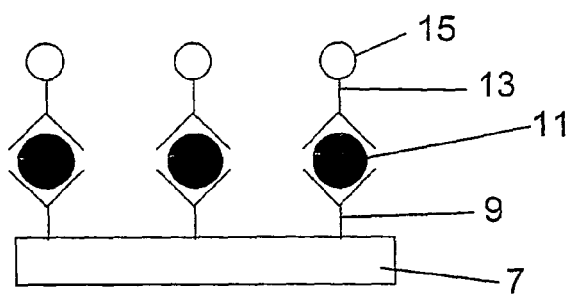
FIGS. 1A, 1B and 1C show details of a substrate provided with binding sites able to selectively bind target sample, and conductive labels being directly or indirectly bound to the target sample in different ways.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The present invention will mainly be described with reference to detecting target DNA sequences but the present invention has wider application than only DNA detection.

The present invention provides a method for measuring the presence of target substances such as target molecules or materials, especially target biological molecules and materials, which allows quantified detection of the presence of target substance on a substrate. In one aspect of the present invention, the method comprises the steps of binding a target sample to selective binding sites on the substrate, whereby the target sample is directly or indirectly labelled with labels, and carrying out a capacitive detection of the presence of the bound conductive labels. The capacitance measurement is preferably carried out between insulated electrodes.

The labels, in one aspect, can be conductive labels. The conductive labels can for example comprise a metal, e.g. a gold nanoball or microball on which a conductive substance such as a metal is deposited or precipitated, e.g. silver, a semiconductor (such as e.g. carbon nanotube or polymer), or the labels may comprise a conductive molecule, a magnetic or ferromagnetic component, a substance opaque to some specific wavelength, or any material whose physical presence can change the capacitance measured between two electrodes, e.g. by varying the effective insulation distance between or the effective insulation area between the electrodes. The labels may also be any material which allows generation of a conductive label, e.g. a molecule which can initiate silver deposition. Preferably the labels are bound in real-time without disturbing the binding of the target substance.

With the present lithographic procedures known from semiconductor manufacture, electrodes of a sensor device can have a width of about 2 to 1 µm and be spaced 2 µm to 1 µm apart. In that case, the conductive labels preferably have a diameter of at least 400 to 800 nm (i.e. between 30% and 80%, preferably about at least 10% of the spacing between two neighbouring electrodes). If the labels are smaller than this size, or are non-conductive, the labels are preferably enlarged to conductive labels of about that dimension e.g. by silver precipitation, in order for a single bound target substance to be detectable. According to the present invention, a single grain only has to develop up to a size of between 400 nm and 1.5 µm, preferably to a size of between 600 nm and 800 nm, in order to allow a single grain to be detected.

The change of capacitance during binding of the labelled target molecules and/or during subsequent metal deposition may be measured continuously or intermittently. Because the electrodes have a non-conductive surface, no DC current and only very small AC current is flowing and thus the solution will not be influenced by the measurement.

Figure 1B:
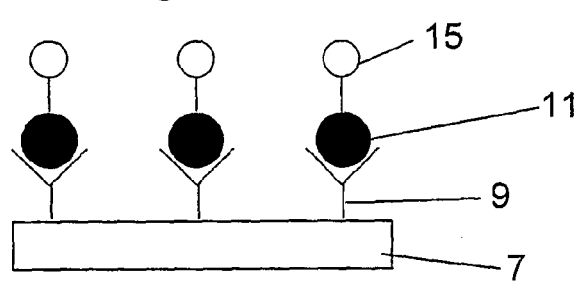
Figure 1C:
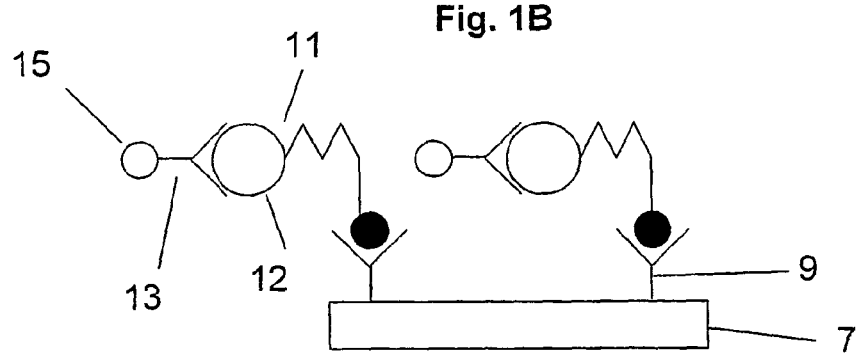

As shown in FIGS. 1A, 1B and 1C, a substrate 7, is itself able to bind selectively a target sample 11 in one aspect of the present invention. Suitable materials for selective binding of target samples 11 without requiring additional materials can be found in "Diagnostic Biosensor Polymers", A. M. Usmani et al., Am. Chem. Soc. 1994. The substrate 7 may also be provided with binding sites 9, such as for example binding molecules or antibodies, able to selectively bind a target sample 11 such as for example a target molecule species or an antigen. Any biological molecule that can be coupled to a matrix is of potential use in this application. It will be understood by the skilled person that a specific substance may be used at a binding site to detect a target substance or vice versa, i.e. the target substance can be used at the binding site to bind binding substance, in this case the two substances change their roles. Examples of the target molecule or the binding molecule are:

Nucleotide sequences: DNA, RNA double or single stranded or DNA-RNA hybrids, with or without modifications, attached as such to a matrix or attached via a spacer molecule.

Proteins or peptides as well as other complex structures formed from amino acids e.g. antibodies, DNA or RNA binding proteins.

Other biological molecules such as oligo- or polysaccharides or sugars.

Portions of cellular material such as cell membranes, which may include receptors, or isolated membrane receptors.

Small molecules, such as inhibitors, ligands, pharmaceuticals, toxins, herbicides, pesticides bound as such to a matrix or attached via a spacer molecule.

The items spotted on the grid will be most likely libraries of compounds, such as peptide/protein libraries, oligonucleotides libraries, inhibitor libraries.

There exist different possibilities to connect labels 15 to the target sample 11, examples of which are shown in FIGS. 1A, 1B and 1C.

In FIG. 1A, a sensor substance 13 labelled with one or more labels, e.g. conductive labels 15, is able to selectively bind to a target substance 11 when this is selectively bound to the binding or capture substance 9. For example, when the target substance 11 is a protein, an antibody labelled with a conductive label 15 and specific to a first epitope on the protein can be used as the label combination 13, 15. A second antibody specific to a different epitope can be used for the binding molecule 9. Both monoclonal and polyclonal antibodies may be used. As shown in FIG. 1A, conductive labels 15 are indirectly bound to the target sample 11.

In FIG. 1B, the target sample 11 molecules are directly labelled by, for example, conductive labels 15. The conductive labels may be applied to the target molecules by means of a spacer molecule, e.g. attached to a biotinylated DNA target molecule.

In FIG. 1C, target sample 11 is labelled by first labels 12. Such a labelled target sample 11 (e.g. biotynilated DNA) is selectively bound to binding sites 9. An example of a conductive-labelled sensor molecule 13 comprises a sensing agent, e.g. streptadivin, labelled with a conductive label 15. The sensing agent is able to selectively bind to the biotin label 12 on the target sample 11. In this case again, the labels, e.g. conductive labels 15 are indirectly bound to the target sample 11.

According to an embodiment of the present invention, detection is carried out by capacitive measurement between pairs of electrodes, the sensitive area of each electrode being insulated with an electrically insulating layer, e.g. passivated with an insulating surface, e.g. the electrode is aluminium and is anodised or oxidised, or coated with an insulating material such as a paint or a lacquer. The complex impedance through this insulating layer and surrounding materials (liquid or air) is measured.

Due to the insulating layer, an efficient protection is provided against chemical attacks that occur during support preparation and DNA revealing. Requirements for the passivation layer are the following: chemical and mechanical robustness, chemical stability, and high dielectric constant to increase the sensing dynamic and sensitivity. Furthermore, electrode deposition and formation as well as the passivation thereof is preferably easy to introduce into standard IC semiconductor processing, e.g. into a CMOS process.

The electrodes may be made e.g. of a metal which is a non-noble metal, such as aluminium or copper or any other conductive material that is compatible with integrated circuit fabrication, especially one which is not a noble metal. The insulating layer may be an oxidised or anodised layer thereof or the separate deposition of an insulating layer. The insulating layer should preferably have a good electrical strength allowing a low thickness and a high dielectric constant. Preferably, an electro-chemical or plasma-assisted process (anodising) is used to grow an alumina protecting film ($Al_2O_3$) onto aluminium electrodes. Such electrodes with a dielectrically coated or passivated surface are much more compatible with conventional integrated circuit processing than the prior art electrodes based on bare noble metals such as gold or platinum.

One way of manufacturing of the devices may for example be as follows. Firstly, a substrate 20 (FIG. 2) is provided, e.g. a bulk <100> Si wafer with low doping concentration (e.g. boron $1\times10^{15}$ $cm^{-3}$). In embodiments of the present invention, the term "substrate" may include any underlying material or materials that may be used, or upon which a device, a circuit or an epitaxial layer may be formed. In other alternative embodiments, this "substrate" may include a semiconductor substrate such as e.g. a doped silicon, a gallium arsenide (GaAs), a gallium arsenide phosphide (GaAsP), a germanium (Ge), or a silicon germanium (SiGe) substrate. The "substrate" may include, for example, an insulating layer such as a $SiO_2$ or an $Si_3N_4$ layer in addition to a semiconductor substrate portion. Thus, the term substrate also includes silicon-on-insulator (SOI), silicon-on-glass, silicon-on sapphire (SOS) substrates. The term "substrate" is thus used to define generally the elements for layers that underlie a layer or portions of interest. Also, the "substrate" may be any other base on which a layer is formed, for example a glass or metal layer. In the following, processing will mainly be described with reference to silicon processing but the skilled person will appreciate that the present invention may be implemented based on other semiconductor material systems. The skilled person can select suitable materials as equivalents of the dielectric and conductive materials described below.

On top of the substrate 20, an insulating layer 22 is provided, e.g. 400 nm of silicon oxide is grown by thermal oxidation in wet atmosphere, providing the desired isolation and surface characteristics to allow a good DNA single strained bonding (Si—OH terminals). Preferably, this insulating layer is made of a low k material. Ideally, the insulating layer will allow fixation of the molecules to which the target sample will bind. One suitable low k material can be porous silicon dioxide. Then, the electrodes 24, 26 (metal areas) are constructed e.g. using aluminium through lift-off processing, which is best to protect the surface of the insulating layer 22. Finally the electrodes 24, 26 are protected from the possibility of being chemically etched during DNA attachment or damaged during manipulation, by a passivation layer. This passivation layer may be formed e.g. by anodising or by oxidising the underlying metal. Alternatively, other insulating layers may be formed, e.g. lacquers or paints or an oxide layer or a nitride layer. For example in the case of aluminium electrodes as mentioned above, these electrodes may be anodised using an electrochemical processing, to form e.g. a 100 nm thick aluminium oxide. Finally, the back sides of the wafers can be (it is not required in all cases) finished, thus eliminating the residual silicon oxide and adding aluminium for the contact to allow the measurement of the MOS capacitance.

Figure 3:
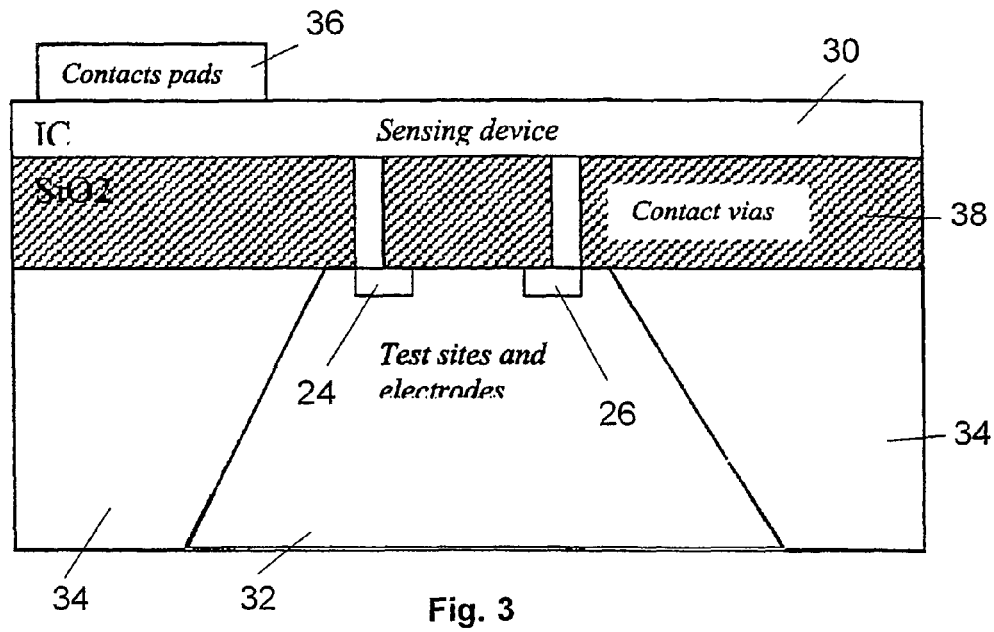
FIG. 3 shows a cross-sectional view of an embodiment of a sensor device IC.

The use of a silicon-on-insulator (SOI) wafer with thin-film devices offers decoupling of the processing of an integrated circuit 30 for controlling the measurement (on one side of the wafer) from the formation of the sensing electrodes 24, 26 (on the other side of the wafer, after micromachining a cavity 32 in the underlying silicon substrate 34), as illustrated in FIG. 3. Major advantages of such solution are that the processing of the IC 30 can be performed completely separately from the test sites surface and electrodes 24, 26. The chip 30 can be externally contacted at contact pads 36 without interfering with the biological test sites (e.g. by flip-chip packaging). The test site surface for DNA binding can be plain thermal or porous silicon dioxide or another insulating layer (more general) 38 with excellent binding properties (which is less easy to achieve on the IC side of the chip). Binding of molecules to silicon oxide and porous silicon oxide is described in "Genomic fingerprinting using oligonucleotide arrays", by Kenneth L. Beattle, in "DNA markers", ed. G. Caetano-Anolies and P. M. Gresshof, Wiley-VCH, 1998. The micromachined cavity 32 can be closed by another substrate (e.g. glass, silicon—not represented in FIG. 3) with micromachined reaction chambers and other microfluidic devices to form a lab-on-a-chip solution.

All the processes and materials mentioned hereinabove for the manufacturing of the devices, except for anodising, are normally used in a CMOS technology, making the device compatible with it and at low cost.

One way to reduce the cost can be to use a thin-film transistor (TFT) MOS process (i.e. polysilicon transistors on glass such as used in flat panel display manufacture, whose performance is compatible with the circuits to be developed, but which enables larger chip sizes at lower cost).

Figure 2:
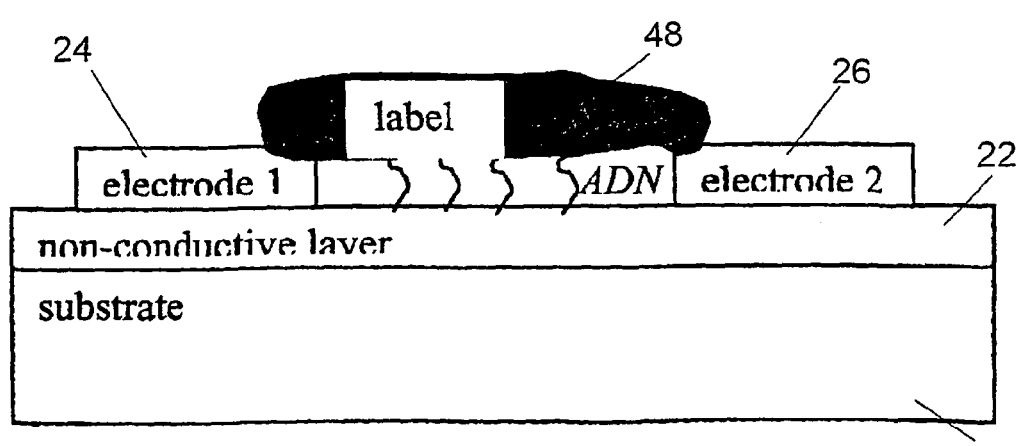
FIG. 2 is a vertical cross-sectional view of (a part of) a capacitive sensor device according to an embodiment of the present invention.

A vertical cross-section of a detector according to the present invention is shown in FIG. 2. The electrodes 24, 26 may for example be interdigitated electrodes, an array of parallel fingers which can be addressed pair-wise, a matrix of point electrodes which can be individually addressed in pairs, or an array of crossed fingers whose intersections can be individually addressed.

Figure 4:
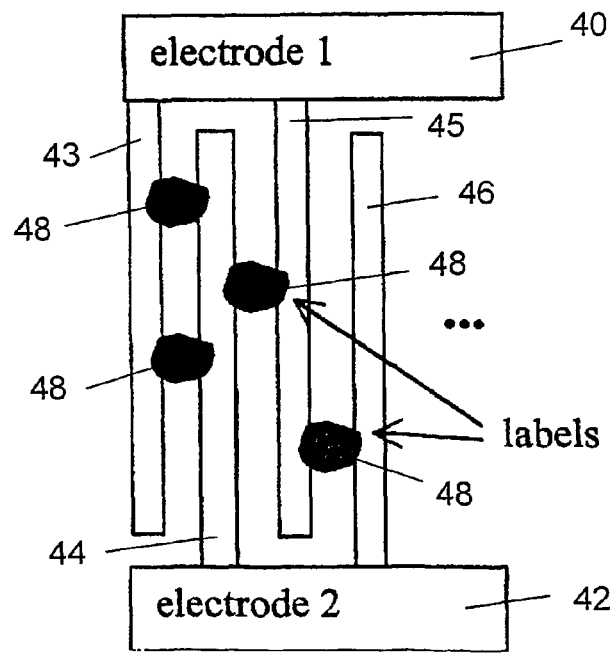
FIG. 4 is a schematic top view of (a part of) a capacitive sensor device according to an embodiment of the present invention.

A top view of an array of interdigitated electrodes 40, 42 with parallel fingers 43, 44, 45, 46 is shown in FIG. 4. All fingers 43, 45, resp. 44, 46 related to one electrode 40 resp. 42 are short-circuited. With the present invention, the interdigitated electrodes 40, 42 can be arranged to cover the whole spot area. In this case, multiple contact points between the electrodes 40, 42 and conductive labels 48 are obtained and simultaneously measured.

Figure 5:
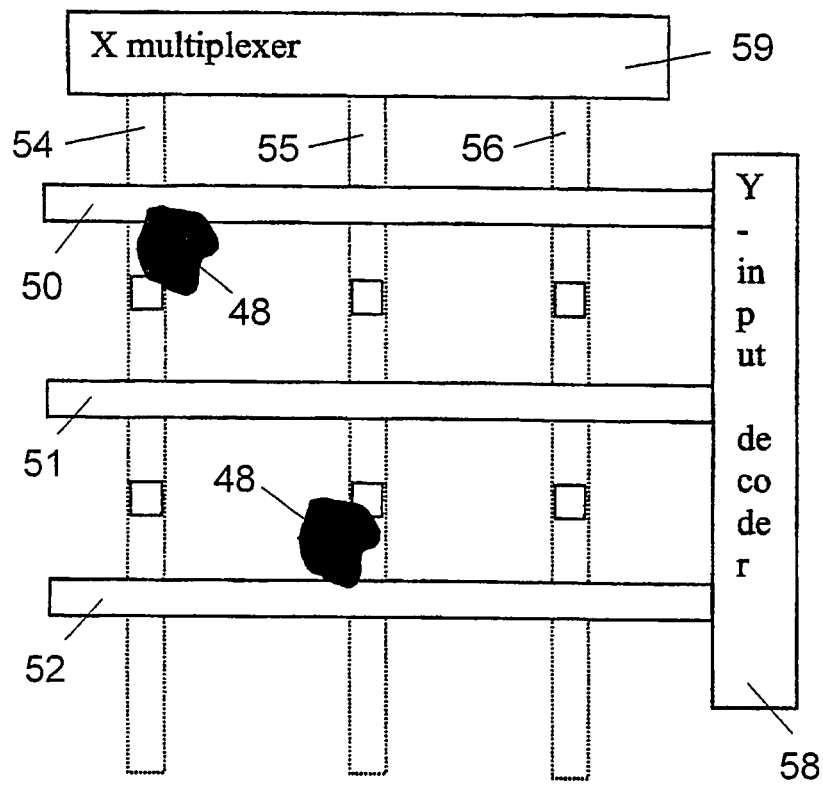
FIG. 5 is a schematic top view of an array of crossed fingers whose intersections can be individually addressed by pairs, according to an embodiment of the present invention.

A top view of an array of crossed fingers 50, 51, 52, 54, 55, 56 whose intersections can be individually addressed by pairs is shown in FIG. 5. In this case, an input test signal is applied on a single line 50, 51, 52 selected through an Y decoder 58, and the output signal is read either on all X lines 54, 55, 56 simultaneously through specific interface circuits (not represented), or on one X line or a number of X lines sequentially, the X lines being selected through an output X multiplexer 59.

This embodiment is more complex to manufacture than the embodiment of FIG. 4, as two levels of metal are required, as well as integrated matrix decoders, selectors and read interface circuits. An advantage is that ultimately the reading can turn digital-like, i.e. it can be tested if a label 48 is present at each site and the number of labels 48 can be counted to quantify the hybridisation. Furthermore, a possibly degraded part of the matrix can be detected and discarded prior to hybridisation.

Figure 6:
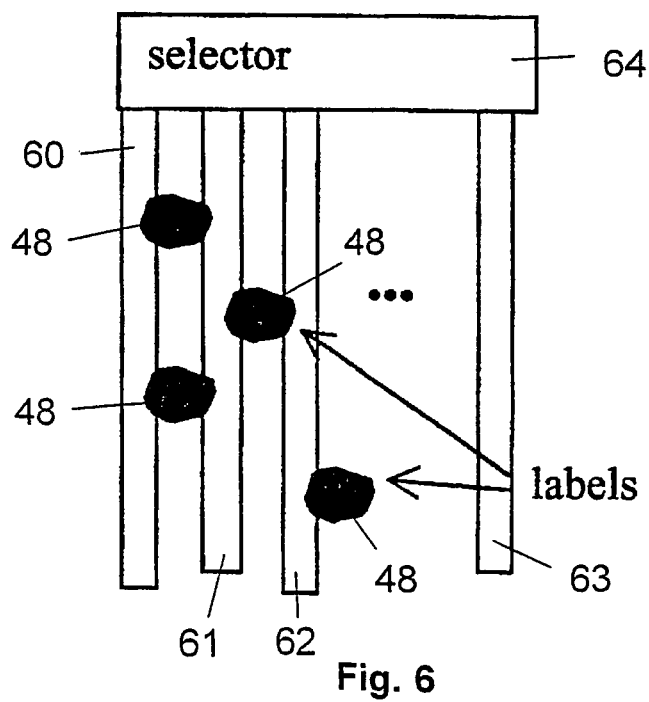
FIG. 6 is a schematic top view of an array of parallel fingers that can be addressed by pairs, according to an embodiment of the present invention.

FIG. 6 is a schematic top view of an array of parallel fingers 60, 61, 62, 63 which can be addressed by pairs by means of a selector device 64. This is an intermediate solution of the embodiments of FIG. 4 and FIG. 5. Long lines are used as in FIG. 4, however, they are not short-circuited at both ends, but they are addressed by pairs by means of a line selector 64. A line selector 64 can be present at one end (as in FIG. 6) or at both (as in FIG. 7). This embodiment only requires a single level of metal, contrary to the embodiment of FIG. 5, but still a malfunctioning part of the array can be discarded.

An advantage of this type of detecting arrays is that a type of "sliding measurement" can be carried out: at low levels of hybridisation and labelling, the measurement can be done between closely spaced electrodes, whereas at high levels of hybridisation, wider spaced pairs of electrodes can be selected to avoid saturation of the measurement.

It is to be noted that the matrix arrangement of FIG. 5 can be configured through dedicated selectors to combine two digitated structures as in FIG. 6, one in each direction of lines X or Y, with point measurements at each X or Y location.

It is also possible to individualise the contact electrode points of the lines X and Y, i.e. isolate each of them from the interconnect line itself, by accessing each point of the matrix e.g. through an array of MOS transistors whose gates are driven by signals applied on interconnect lines.

Figure 7:
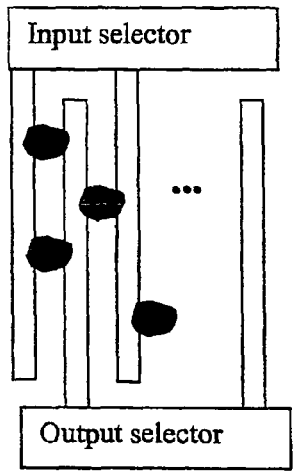
FIG. 7 is a schematic top view of an array of interdigitated fingers that can be addressed by pairs, according to an embodiment of the present invention.

The interdigitated structures as in FIG. 4 and FIGS. 6-7 are simple, low-cost, and efficient means to achieve capacitance-like sensing. To maximise the sensitivity, the size of the electrodes fingers (width+spacing<5 μm) is preferably in the same order of magnitude as the width of the active silver layer obtained by silver precipitation e.g. as initiated by gold nanoballs, resulting silver domains of about 0.5-1 μm in diameter. The size of silver domains necessary to test is preferably kept small so that long development time is not required. The electrodes can be realised e.g. on glass or Si. In the Si case, to avoid a direct current passing through the bulk substrate 20, the electrodes 24, 26 are insulated from the doped silicon substrate 20 by a silicon dioxide layer 22. The thickness of this oxide (e.g. 400 nm thermal wet oxide) is chosen as high as possible to minimise bulk effects, but still compatible with a short process time.

Figure 8:
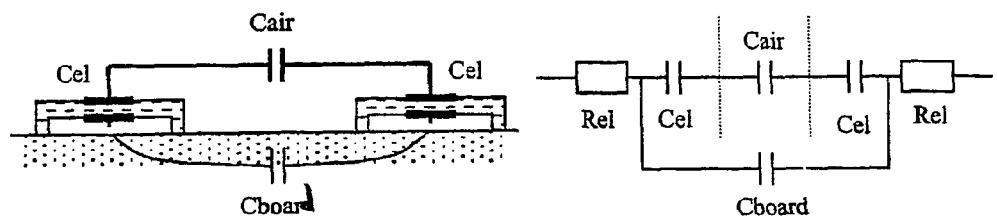
FIG. 8 shows an equivalent electrical circuit of a sensor device according to the present invention in case of no DNA binding.

Due to this support structure, the capacitance measured in the case of no DNA binding includes only the parasitic capacitance of the support (Cboard) and the contribution of the fluid, e.g. air or liquid, surrounding the fingers. (The drawing FIG. 8 shows also the small resistance Rel of the fingers but this can usually be ignored).

Figure 9:
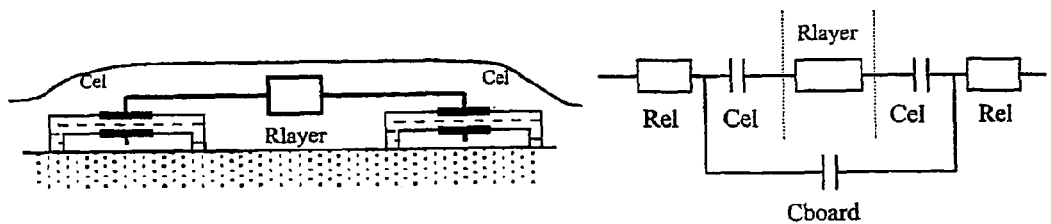
FIG. 9 shows an equivalent electrical circuit of a sensor device according to the present invention after DNA hybridisation.

After the DNA hybridises and e.g. silver label precipitation, the passivation capacitance Cel is taken into account in the equivalent circuit (FIG. 9), connected in parallel with the parasitic capacitance by means of the conductive labelled layer (Rlayer resistance).

Simulated by a lumped circuit RC-series scheme, the above model presents a frequency dependence with three distinct regions:

at low frequencies, the impedance of Cel dominates the layer resistance and the global measured capacitance is the sum of half the passivation capacitance and the parasitic one;

at high frequencies, the biggest part of the current flows into the low-impedance parasitic capacitance, and the measured values stabilise at Cboard;

around an intermediate frequency, the global impedance becomes mainly resistive (silver layer resistance).

As the intermediate frequency is a function of the layer resistance, a frequency detection with very high sensitivity can be considered (impedance or capacitance spectroscopy).

Before the precipitation of the metallic labels, Rlayer is infinite. With precipitates, the physical presence of the labels reduces Rlayer according to the density of the labels and hence, according to the level of hybridisation.

A detector according to the present invention does not measure a change of an electrical parameter due to a change of the dielectric properties of hybridised DNA alone. According to the present invention, a conductive label is introduced whose presence affects the capacitance of the medium between the electrodes. Or, in other words, the change of capacitance is not dictated by a change of permittivity of the medium between the electrodes, but by a change of the physical dimension or separation between the electrodes caused by the formation of a conductive part.

The capacitive detector is well adapted to the miniaturisation of the proposed test sites. The distance between two electrodes is reduced to a dimension comparable with the size of a single conductive or metallic label (e.g. 0.5 µm to 1 µm in the case of Ag precipitates, potentially smaller in other cases). The measurement of capacitance may be made by any suitable technique, e.g. application of a steady state sinusoidal voltage and measurement of current and voltage or application of a voltage step function and measurement of the dynamic response. In a preferred embodiment, a specific signal is applied to one electrode and the resulting signal is monitored at the other electrode of a pair. The advantage of short-distance electrodes is that the hybridisation and labelling of a single DNA strand with a conductive label is sufficient to record a change in capacitance value between the electrodes.

Figure 10:
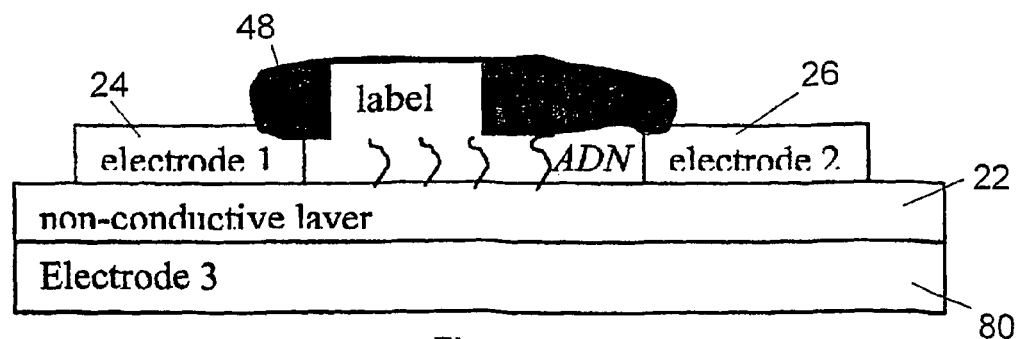
FIG. 10 is a vertical cross-section of another embodiment of a detector according to the present invention, in which a third electrode is provided underneath a non-conductive layer.
Figure 11:
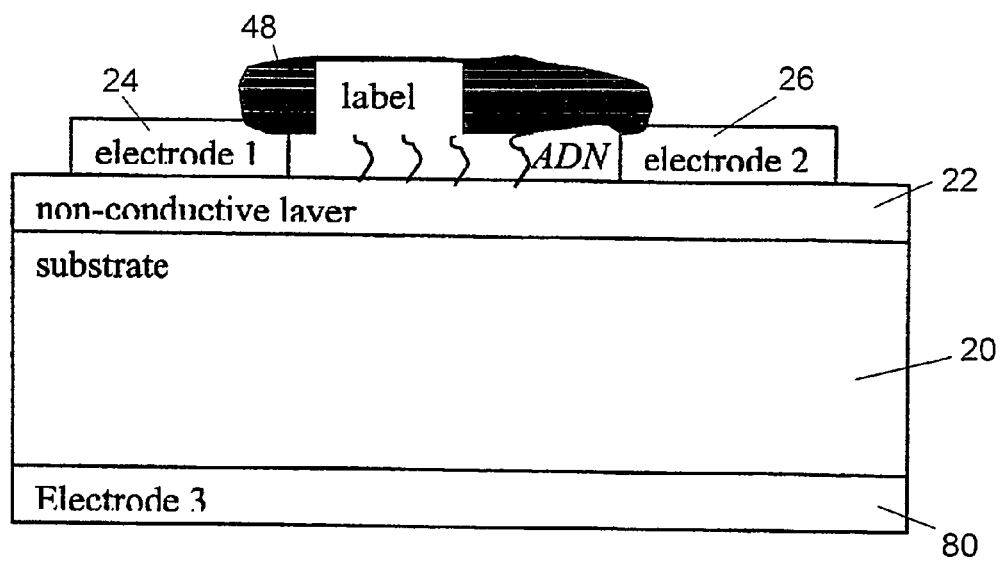
FIG. 11 is a vertical cross-section of another embodiment of a detector according to the present invention, in which a third electrode is provided underneath a substrate.

According to a further embodiment of the present invention, as shown in FIG. 10 and FIG. 11, a third electrode 80 can be built below and insulated from the two previous electrodes 24, 26. In this case, the capacitive measurement done between the first electrode 24 and the second electrode 26 can be complemented by a capacitance measurement performed between the third underlying electrode 80 and one electrode out of the first electrode 24 or the second electrode 26 or both in short-circuit. Again the capacitance value measured between first or second electrodes 24, 26 and third electrode 80 will change considerably by the presence of the conductive label 48, which adds to the effective area of the capacitor. If no labels 48 are present, the effective coupling area is limited to the electrode designed overlaps. If labels 48 are present, their area adds to the overlap. To increase the discrimination, the insulating layer 22 between the third electrode 80 and the top electrodes (first electrode 24 and second electrode 26) can be structured to be thicker under the first and second electrodes 24, 26 (hence yielding smaller capacitance) and thinner under the labels 48 (hence yielding larger capacitance).

According to an embodiment of the present invention, capacitance between two electrodes of a capacitive sensor device may be measured as a function of frequency. The result shows three zones:

at low frequencies, a capacitive behaviour with a high value related to the thickness of the dielectric lying on top of the electrodes, at intermediate frequencies, a resistive behaviour, the value of which is related to the resistivity of the conductive layer, at high frequencies, a capacitive behaviour whose low value corresponds to the initially calibrated value (i.e. without any label).

A full frequency response therefore yields much more information about the label density than the pure DC capacitance measurement.

According to a further embodiment of the present invention a multi-sensor technique is implemented (it is to be noted that this is also already the case with the three electrodes of FIGS. 10-11 which enable the measurements of two capacitive signals), in which different signals can be read out of the same test sites using at least one supplementary excitation and reading next to the capacitive measurement. The different output signals can be correlated to reject noise and to enhance the global sensitivity.

A single structure such as e.g. a MOS transistor or even a simple diffused resistor, located in the substrate 20 of FIG. 11 or in the layer 30 of FIG. 3, can become a multiple purpose sensor obtaining different signals from the same labelled DNA, when submitted to different excitations, if the labels have at least two of the three following properties:

If the labels are conductive, they can form an effective gate on top of the gate dielectric which can be electrically coupled to the top electrodes 1 or 2 (FIG. 11), thereby changing the conductivity of the underlying semiconductor device.

If the labels are magnetic, Hall effect will develop into the semiconductor and effective conductivity will be affected as well.

If on the contrary the labels provide an effective shield against an external magnetic field, its absence could be sensed when the DNA is hybridised and labelled.

If the labels are opaque, light will generate excess carriers in the semiconductor device if DNA is not hybridised, thus changing the conductivity. For example CMOS compatible photodetectors may be used, which are covered by silicon oxide on which DNA may be immobilised. Gold nanoparticles and silver precipitation may be used to get a dense opaque layer revealing the hybridised DNA. Measurements are carried out before and after DNA hybridisation, or better versus a reference photodetector of the same chip which never undergoes DNA hybridisation or labelling, with exactly the same light exposure conditions. The difference of photocurrents measured is directly linked to the opacity of the silver layer and thus to the DNA hybridisation.

if the labels are radioactive, the presence of the labels can be determined by measuring radioactive emissions using a Geiger counter or exposing a sensitive film such as a photographic film to the emitted radiation. On developing the film; the location of labels can be determined.

In a detection technique according to the present invention, based on conductive labels that change the capacitance between two electrodes, a number of instrumentation circuits can be implemented to convert the capacitance variation information in a voltage or current easier to process:

A basic circuit comprises an active opamp inverting configuration with an input capacitor and a feedback capacitor (one of which being the capacitance under test, the other a fixed capacitance value) in which the output voltage is given by the input voltage multiplied by the ratio of the input capacitance to the feedback capacitance. In this case, such a circuit would most probably be used as a line or column detector at the end of e.g. each line of the XY matrix of FIG. 5 or with a multiplexer for a set of lines. The resolution is maximal if the fixed capacitance can be chosen according to the level of hybridisation (i.e. close to a value equal to that of the unknown capacitance) or if the input voltage can be adapted similarly.

Another basic circuit comprises a fixed current source charging the unknown capacitor during a given time and a reset device which discharges the capacitor periodically, the output voltage on the capacitor at the end of the charging period being a function of the fixed bias current. It can be read using of pixel amplifier for each individual test sites as in a CMOS camera APS circuit. It is then possible to adapt the charging current or period to the level of hybridisation (i.e. the value of capacitance) so that to enhance the resolution. Double sampling, correlated double sampling and other techniques can also be implemented to suppress the influence of errors due to noise, offsets, etc.

A third circuit is similar to a DRAM architecture, i.e. each test site can be connected to a bus line through a switch. When the switch is activated, the test site capacitance can be written or read. The difference with a DRAM is that here the capacitance does not have a fixed constant value. However this can be measured by monitoring the level of the signal which must be supplied to the bus line to read or write the cell. In this case, current-sensing techniques can be most powerful.

A number of test site capacitances can be arranged as a bank of series or parallel capacitances which are addressed simultaneously as in ADC techniques to determine levels of signals to be compared to threshold values to directly generate a binary word representing the analog signal. In ADCs, the input signal is unknown and the capacitances are constant; here a known signal would be supplied to unknown capacitances.

It is to be noted that the above instrumentation circuits are compatible with the acquisition, at high speed, of many successive measurements, during the evolution of the reactions, yielding time-varying signals which can then be processed by adequate algorithms to enhance the noise rejection and hence sensitivity and specificity of the detection.

Furthermore, the performance of all these read-out circuits will be significantly better in the SOI technology mentioned above, than in any comparable other CMOS process.

EXAMPLE

Materials and Processes

Standard P-doped Si wafers were used to make the chips according to the present invention. In order to insulate the electrodes from the substrate and lowering the parasitic bulk effects, a 400 nm thick thermal wet oxide ($SiO_2$) was grown—in fact previous experiments showed that this kind of material enhanced the binding of DNA to the support. The growing temperature and time of the $SiO_2$ were 1000° C. and 1 h 16 min respectively. To guaranty a pure wet oxide, a short delay of around 1 minute only was left between oxygen and hydrogen valves opening.

The electrodes were manufactured with pure aluminium, by means of a lift-off process. This was preferred to an etching method because previous tests used to show a non-specific silver precipitation on a 240 nm-thick silicon oxide in the second case, after deposition and plasma etch of 1 μm of {Al+2% Si}. In the lift-off process, an aluminium thickness of 500 nm was used, and nitric acid was used for the photoresist etching.

At the backside, the chips were also covered with pure aluminium (300 nm thick) to ensure a good electrical contact to the bulk.

Finally, an electrolytic anodising method was used to passivate the chips which implies the manufacture of cathodes. For example, one cathode consists of a simple wafer covered with aluminium on both sides (500 nm and 300 nm at the front and back respectively).

With regard to the anodising process, an electrolyte as cited hereinafter was used:
solvent glycol ethylene (OH—CH2-CH2-OH): 1 litre
boric acid (H3BO3): 237 g
ammonium hydroxide, conc. 30% (NH4OH): 89.5 ml The wafers containing the chips to be oxidised were placed parallel in front of the cathodes with a gap of 3 cm. The operating current density was fixed at 1 $mA/cm^2$, and a maximum voltage of 73 V was chosen to obtain a 100 nm thick aluminium oxide. The connection of the wafers to the external positive slot of the generator was done by mean of a clip, put on a global supply pad near to the flat. All the chips are connected to it (FIG. 1).

The Sensors

Figure 12:
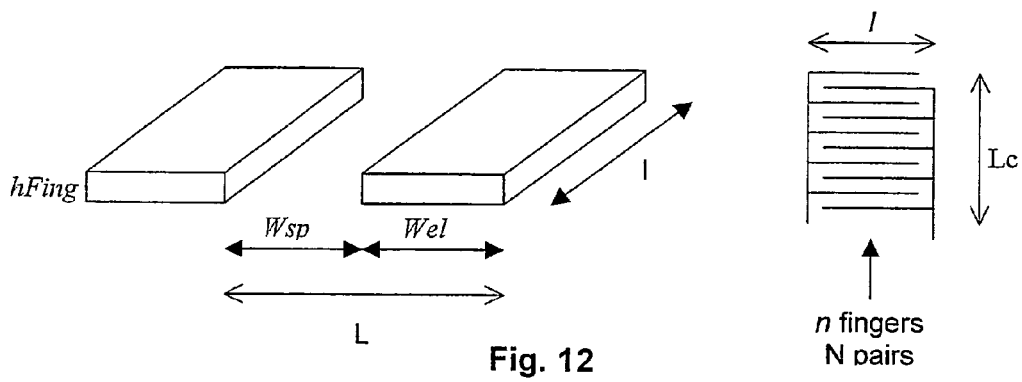
FIG. 12 shows the notations of dimensions of sensor and fingers of interdigitated electrodes, which dimensions are used for explaining the experiments.

The notations of the interdigitated electrodes' dimensions appear in FIG. 12. The height of the fingers is hFing=500 nm. The total size of a sensor is Lc=l=400 μm (diameter of a robot spotting plot), and all the sensors tested had equal fingers' width and spacing: Wel=Wsp.

3 characteristic lengths of the sensors were: L=2 μm, 4 μm and 6 μm. This corresponds to fingers' widths and gap Wel=Wsp=1 μm, 2 μm and 3 μm respectively.

Figure 13:
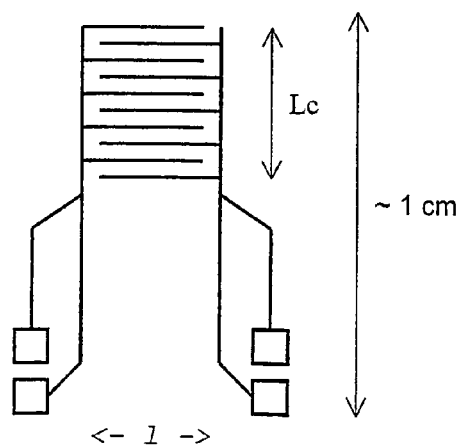
FIG. 13 is a schematic view of an interdigitated sensor with access lines and contact pads in a four-points architecture.

The tested Biochips were 1 cm long and 2 mm large. Three sensors were placed on a chip on one end and connected to the bonding pads on the other. Since the measurement used a four point method, there are two lines and two connecting pads per electrode, as shown in FIG. 13—i.e. 4 lines and pads per sensor, or 12 for an entire chip. The long connection lines were 30 μm large and the pads had sizes of 200×200 $μm^2$. All these additional areas were also passivated.

Measurements and Results

To perform the measurements, an RLC-meter HP4275A with built-in RC-series extraction mode was used. The test set-up worked with a 4-probes method to eliminate the parasitic elements of the connecting lines, which is well adapted to the 4 bonding pads of the biosensors according to the present invention. The experiments were carried out in the dark in a metallic cage; the external slots of the cage were connected to the inputs/outputs of the HP RLC-meter by means of simple 50Ω coaxial cables, about 1 meter long.

The voltage amplitude of the oscillator (0 to peak), used by the HP RLC-meter to inject the sensing current, was adjusted to Vosc=100 mV to maximise the precision while lowering the parasitic bulk effects, which appears as a modulation of the depletion/inversion layer under the electrodes.

The presence of DNA was detected after revealing with gold nanoparticles and silver amplification. Silver precipitation over the electrodes built a metallic bridge either partially or completely between the insulated fingers, also giving access to the capacitance of the passivation layer. Tests were performed with 2 DNA concentrations (+witnesses for false readings) and 2 amplification times.

Figure 14:
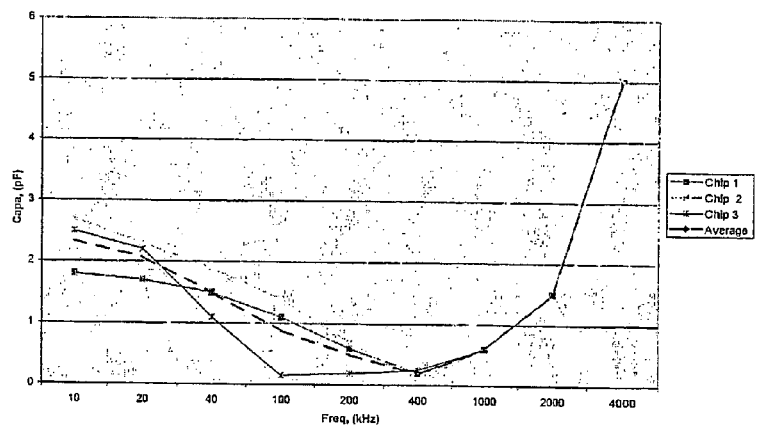
FIG. 14 is a graph of the capacitance of 3 opened sensor devices according to the present invention in function of frequency.

As a calibration method, 3 measurements have been first completed on the "opened" structures where no interdigitated fingers were present, i.e. that contained only the access lines and bonding pads. The average of these 3 curves gave a calibration reference (dashed line on FIG. 14). With this method, the parasitic capacitance of long lines, bonding pads, and access cables were then subtracted from all the results before exploitation. FIG. 14 illustrates the calibration results obtained.

Figure 15A:
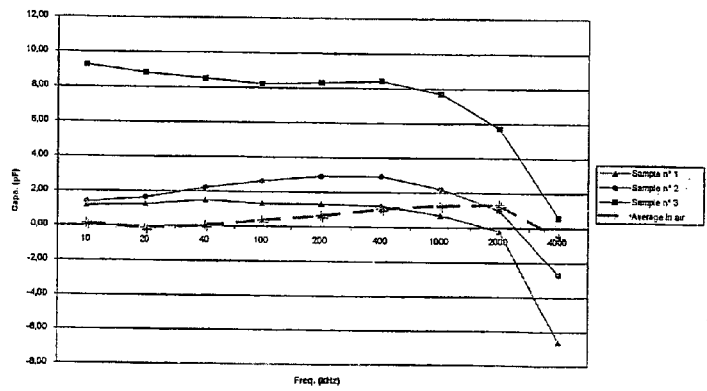
FIGS. 15A, 15B and 15C are graphs showing the capacitance of sensor devices in function of the frequency.
Figure 15B:
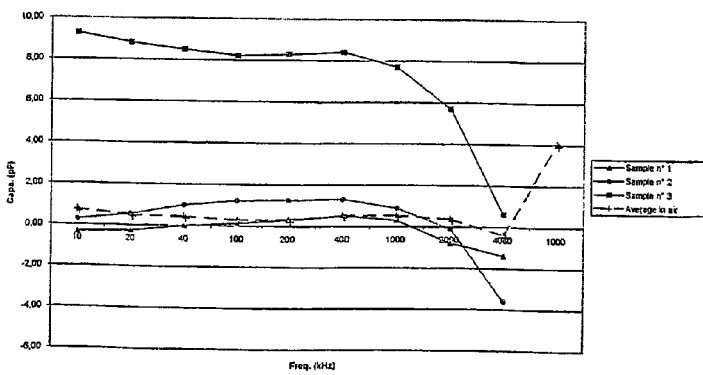

In order to compare the results from no DNA to full silver precipitation, the same kind of measurements have also been done in air on each type of sensor—L={2, 4, 6} μm, using 3 samples each time. Also, an average of these 3 curves constitutes a first reference per sensor (dashed lines on the graphics, FIG. 15).

It is to be noted that the bulk potential was maintained to Vb=0V during all the experiments by connecting it directly to the shield of the HP4275A.

A total of 6 Biochips were exposed to silver. The following table summarises the DNA concentrations used and the exposure times to silver. The control samples were samples which were not hybridised with DNA but put anyway into the silver revealing solution to control the background noise of the experiment.

| Chip Sample number | 1 | 2 | 3 | 4 | 5 | 6 |
|---|---|---|---|---|---|---|
| DNA concentration (nMol) | 0 (control) | 0.2 | 20 | 0 (control) | 0.2 | 20 |
| Silver revealing time | 2 min 30 sec | | | 2 min | | |
| Grains' appearance | Crystals | | | Balls | | |

For a revelation time of 2 min 30 sec (FIG. 15A, FIG. 15B and FIG. 15C samples 1 and 3), the sensors with L=2 μm and 6 μm detect a significant shift of the capacitance, between 1 and 10 pF, for concentrations of 0, 0.2 and 20 nMol. The capacitance measured with no DNA (sample 1) is close to the average of the 3 sensors in the air, and small in all cases. When the DNA density is high (sample 3), all the sensors give the same value for the capacitance (~8 pF, see FIG. 15A, 15B, 15C). It is to be noted that this maximum capacitance value may theoretically be higher (~30 pF) but the DNA spot wasn't covering all the area of the sensors.

With regard to sensitivity, small structures—with L=2 μm—offer a higher discrimination between the three concentrations. This can be justified by the fact that small fingers scan a thinner layer over the surface and can detect a smaller quantity of silver grains between them.

Figure 15C:
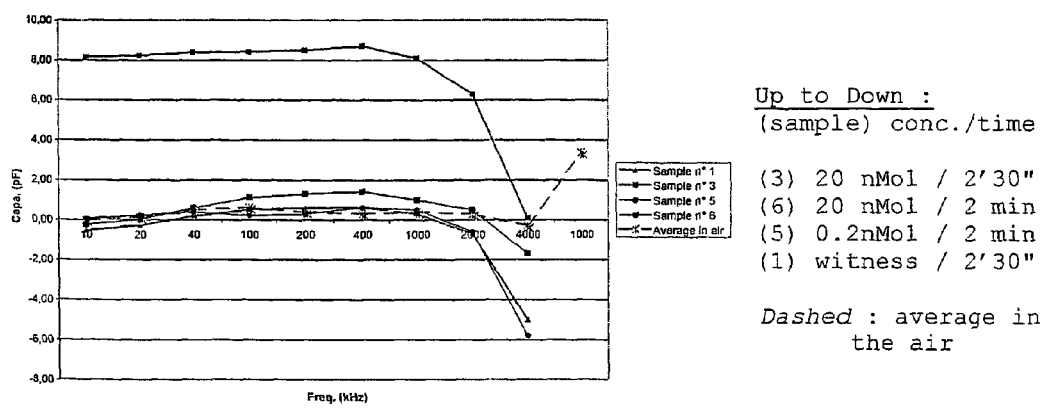

On 4 μm structures, there are no complete results for a 2 min 30 sec revealing but it has been verified at least that the higher capacitance obtained is the same. FIG. 15C illustrates the fact that a short revealing time of 2 minutes is not sufficient to detect a significant modification of the capacitance (samples 5 and 6).

The present invention exhibits one or more of the following advantages. The use of labels, much larger than the original targets, makes the apparatus and method from the fabrication constraints linked to the nano-dimensions of the target molecules themselves such as DNA, and allows the use of a less advanced processing technology, with a subsequent lower cost. The labels change the physical nature of the target neighborhood and the interference caused by this change of the geometrical gaps separating the electrodes affects the capacitance.

The use of labels having a second property, in addition to being conductive, e.g. being opaque, permits investigation by complementary detection methods such as optical detection methods and devices. In accordance with embodiments of the present invention several types of sensing principles can be applied (e.g. electrical+pixels+optical).

Interactions between the labels and the electrodes inside the detection region is made safe, e.g. self-precipitation of silver on pure metal for example is avoided.

The methods and apparatus of the present invention are CMOS and biocompatible, e.g. no use of noble metals such as gold but rather the use of a metal such as aluminum. This is achieved by the electrodes of sensors in accordance with the present invention being completely insulated from the solution, and subsequently biocompatible. For example, a dielectric passivation material is used which can constitute a binding layer as well as a detection parameter and protects the electrodes from any parasitic chemical reactions.

Using passivated electrodes with non-ohmic contact to the biological samples eases the detection of conductive labels by capacitive coupling (since there is little or no effect of parasitic contact resistance, electrolyte resistance). The sensors of the present invention also provide addressable pixels arrays.

While the invention has been shown and described with reference to preferred embodiments, it will be understood by those skilled in the art that various changes or modifications in form and detail may be made without departing from the scope and spirit of this invention. For example, although the invention has been described merely with respect to DNA, also other types of molecules, such as proteins, may be detected by a method and device according to the present invention.

The invention claimed is:

1. A method for capacitive detection of the presence of target sample on a substrate with at least a pair of electrodes having a non-conductive surface layer, comprising the steps of:
   (a) binding a target sample to a selective binding site on the substrate, a conductive label being bound to the target sample, the conductive label having a direct or indirect coupling to the target sample; and
   (b) sensing the presence of the bound conductive label to the binding site to thereby determine the presence of the target sample, wherein the sensing step is a capacitive detection that is carried out by contacting the conductive label bound to said target sample to said non-conductive surface layer of said pair of electrodes on said substrate.

2. A method according to claim 1, furthermore comprising, before the binding step, a preliminary capacitance measuring step.

3. A method according to claim 2, furthermore comprising a step of comparing the preliminary capacitance with the capacitance measured during the sensing step.

4. A method according to claim 1, wherein the labels are formed or enlarged prior to or during the sensing step.

5. A method according to claim 1, wherein capacitance is measured as function of frequency to obtain a value representative of an electrical resistive property of the conductive label.

6. A method according to claim 1, wherein a global impedance is measured and the real part of the global impedance is used in addition to the capacitive part.

7. A method according to claim 1, furthermore comprising a step of optical detection of the presence of the label.

8. A method according to claim 1, furthermore comprising a step of magnetic or radioactive emissions detection of the presence of the label.

* * * * *

UNITED STATES PATENT AND TRADEMARK OFFICE
CERTIFICATE OF CORRECTION

PATENT NO. : 7,943,394 B2
APPLICATION NO. : 10/519014
DATED : May 17, 2011
INVENTOR(S) : Flandre et al.

It is certified that error appears in the above-identified patent and that said Letters Patent is hereby corrected as shown below:

Title page, Item (73) under Inventors, replace "Brussels" with --Bruxelles--;

Page 2, under OTHER PUBLICATIONS, in C. Berggren, B. Bjarnason, and G. Johansson, replace "Electroanlaysis" with --Electroanalysis--;

Under OTHER PUBLICATIONS, in P. Van Gerwen et al., replace "Chicogo" with --Chicago--.

Signed and Sealed this
Sixth Day of December, 2011

David J. Kappos
*Director of the United States Patent and Trademark Office*